United States Patent [19]

Iwao et al.

[11] Patent Number: 4,464,371
[45] Date of Patent: Aug. 7, 1984

[54] FIVE-MEMBERED HETEROCYCLIC COMPOUNDS

[75] Inventors: Jun-ichi Iwao, Takarazuka; Tadashi Iso, Sakai; Masayuki Oya, Ibaraki, all of Japan

[73] Assignee: Santen Pharmaceutical Co., Ltd., Osaka, Japan

[21] Appl. No.: 406,241

[22] PCT Filed: Dec. 22, 1981

[86] PCT No.: PCT/JP81/00401
§ 371 Date: Jul. 27, 1982
§ 102(e) Date: Jul. 27, 1982

[87] PCT Pub. No.: WO82/02200
PCT Pub. Date: Jul. 8, 1982

[30] Foreign Application Priority Data

Dec. 29, 1980 [JP] Japan .......................................... 56-67

[51] Int. Cl.³ .................. C07D 277/30; C07D 417/12; A61K 31/425; A61K 31/50
[52] U.S. Cl. ..................................... 424/250; 424/270; 544/235; 548/200; 548/201
[58] Field of Search ................ 548/201, 200; 424/270, 424/250; 544/235

[56] References Cited

U.S. PATENT DOCUMENTS 4,386,096 5/1983 Iwao .................................... 424/270

FOREIGN PATENT DOCUMENTS

| 48763 | 10/1981 | European Pat. Off. . |
| 2434150 | 3/1980 | France . |
| 2438036 | 4/1980 | France . |
| 11547 | 1/1980 | Japan . |
| 22673 | 2/1980 | Japan . |
| 59175 | 5/1980 | Japan . |
| 104275 | 8/1980 | Japan . |
| 71081 | 6/1981 | Japan . |
| 92279 | 7/1981 | Japan .................................. 548/201 |
| 83419 | 7/1981 | Japan . |
| 123914 | 9/1981 | Japan . |

Primary Examiner—Robert Gerstl

Attorney, Agent, or Firm—Frishauf, Holtz, Goodman & Woodward

[57] ABSTRACT

This invention relates to the compound of the general formula [I], process for preparing the compound and antihypertensive agent containing the compound as a main ingredient.

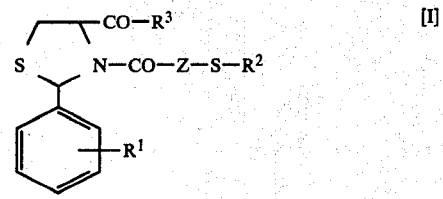

wherein
$R^1$ is hydrogen, hydroxy, lower alkyl or lower alkoxy;
$R^2$ is hydrogen, benzoyl or

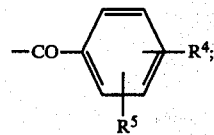

$R^3$ is hydroxy, lower alkoxy, —NHOH or $R^4$ is

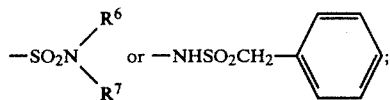 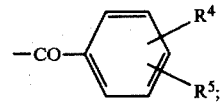
$R^5$ is hydrogen or halogen;
$R^6$ and $R^7$ each is hydrogen or lower alkyl;
Z is straight or branched alkylene containing 1 to 3 carbon atoms;
when $R^3$ is hydroxy or lower alkoxy, $R^2$ is and salts thereof, said lower alkyl and lower alkoxy groups contain 1 to 6 carbon atoms.
17 Claims, 1 Drawing Figure

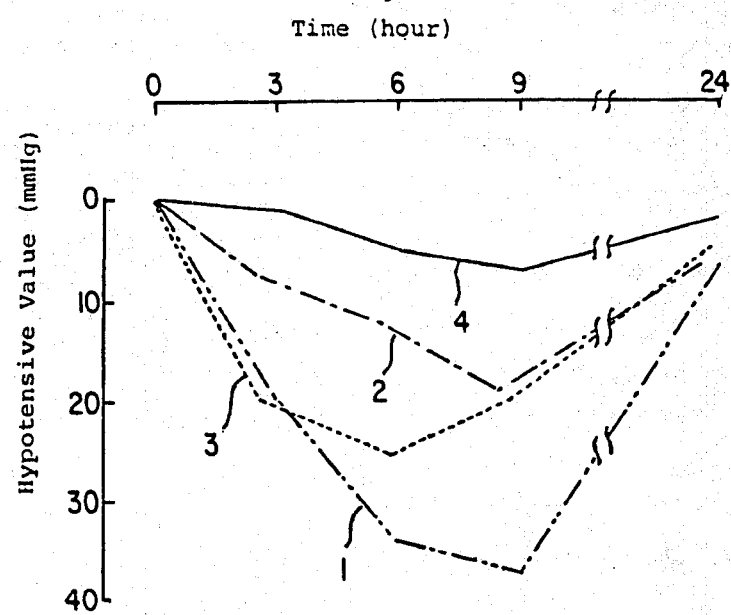

FIVE-MEMBERED HETEROCYCLIC COMPOUNDS

TECHNICAL FIELD

This invention relates to compounds of the general formula [I],

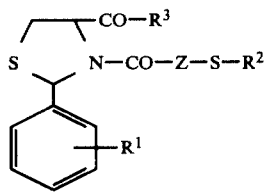

wherein
R$^1$ is hydrogen, hydroxy, lower alkyl or lower alkoxy;

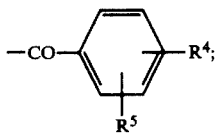

R$^2$ is hydrogen, benzoyl or

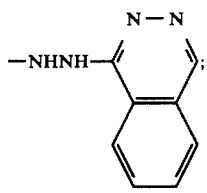

R$^3$ is hydroxy, lower alkoxy, —NHOH or

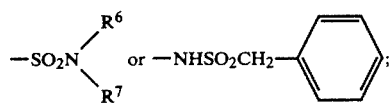

R$^4$ is
R$^5$ is hydrogen or halogen;
R$^6$ and R$^7$ each is hydrogen or lower alkyl;
Z is straight or branched alkylene containing 1 to 3 carbon atoms;

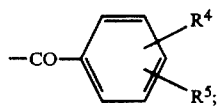

when R$^3$ is hydroxy or lower alkoxy, R$^2$ is
and salts thereof, said lower alkyl and lower alkoxy groups contain 1 to 6 carbon atoms.
The same shall be applied hereinafter.

BACKGROUND OF THE TECHNICAL FIELD

Thiazolidine derivatives having mercapto group are useful compounds as antihypertensive agents. It is known that particularly the compound of the formula [II], which is the basic structure of the compounds of this invention, shows an excellent antihypertensive effect (Japanese patent application No. 49657/1978).

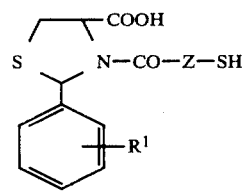

DESCRIPTION OF THE INVENTION

This invention relates to novel thiazolidine derivatives.

We found that the prolongation of the activity and stability of the compound were accomplished by conversion of mercapto group and/or carboxy group of the compound of the formual [II], which shows an antihypertensive effect, into suitable derivatives shown in this invention.

Substituents of the compound [I] of this invention are as follows. Lower alkyl is alkyl group having 1 to 6 carbon atoms, for example methyl, ethyl, hexyl or isobutyl, lower alkoxy is alkoxy group having 1 to 6 carbon atoms, for example methoxy, ethoxy, t-butoxy or hexyloxy, and halogen is fluorine, chlorine or bromine.

The compounds [I] of this invention are synthesized by the following procedures.

The compound of the formula [V] is obtained by condensation of the compound of the formula [III] with the compound of the formula [IV] by the known method such as Shotten-Baumann method, mixed anhydride method, etc.

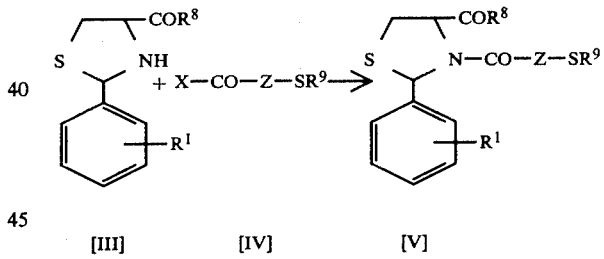

wherein
R$^8$ is hydroxy or lower alkoxy;
R$^9$ is R$^2$ except hydrogen;
X is halogen or hydroxy.
The same shall be applied hereinafter.

The compound of the formula [VII] is obtained by condensation of the compound of the formula [V] with the compound of the formula [VI] by the known method such as mixed anhydride method etc.

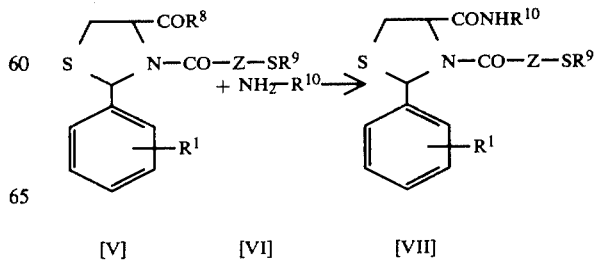

wherein

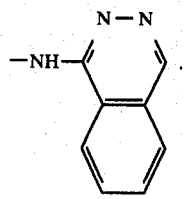

$R^{10}$ is hydroxy or

The same shall be applied hereinafter.

The compound of the formula [I] wherein $R^2$ is hydrogen is obtained by hydrolysis by acid, alkaline, etc.

The compound of the formula [I] prepared by the above methods can form the conventional salts to be generally used as medicine such as sodium salt, potassium salt, calcium salt, magnesium salt, aluminum salt, ammonium salt, diethylamine salt, triethanolamine salt, etc.

The compound of the formula [I] has two or more asymmetric carbon atoms, so it has the stereoisomers, which are within the limit of this invention.

Pharmacological test, acute toxicity test and examples of formulation are shown as below.

PHARMACOLOGICAL EXPERIMENT

Male spontaneously hypertensive rats (Charles River) weighing 370-430 g (37-43 weeks of age) were used.

The subject compound, suspended in 0.5% tragacanth, was given orally to the animals. Their blood pressure was measured by indirect tail-cuff method using a programmed electrosphygmomanometer.

EXPERIMENTAL RESULTS

The FIG. 1 shows the time course of the hypotensive effect in spontaneously hypertensive rats by oral administration of (2R,4R)—3—[S—4—(dipropylsulfamoyl)-benzoyl]—3—mercapto—propionyl]—2—(2-hydroxyphenyl)—4—thiazolidinecarboxylic acid (Example 1) as a representative of the compounds of this invention and of (2R,4R)—2—(2-hydroxyphenyl)—3—(3—mercaptopropionyl)—4—thiazolidinecarboxylic acid as a control compound.

The abscissa of the figure shows the time after administration and the ordinate shows the blood pressure in mmHg having decreased by the administration. In the figure, line 1 and line 2 represent the hypotensive effect by the compound of this invention at doses of 30 mg/Kg and 10 mg/Kg, respectively, line 3 that by the reference compound at a dose of 30 mg/Kg, and line 4 control (no drugs).

The compound of this invention clearly decreased the blood pressure in spontaneously hypertensive rats at doses of 10 mg/Kg and 30 mg/Kg.

It is found from the above pharmacological experiments that the compounds [I] of this invention are useful as the antihypertensive agents with a long-lasting effect.

The compounds can be administered either orally or parenterally. The dosage forms are tablet, capsule, granule, powder, suppository, injection, etc.

For the treatment of hypertension, these preparations can contain not only general excipients but also other antihypertensive agents such as reserpine, α-methyldopa, guanethidine, chlonidine, hydralazine, etc. The dose is adjusted depending on symptoms, dosage forms, etc., but usual daily dosage is 1 to 5000 mg, preferably 10 to 1000 mg, in one or a few divided doses.

ACUTE TOXICITY TEST

Acute toxicity of (2R,4R)—3—[S—[4—(dipropylsulfamoyl)—benzoyl]—3—mercaptopropionyl]—2—(-2—hydroxyphenyl)—4—thiazolidinecarboxylic acid is shown in the table.

TABLE

| Route of administration | $LD_{50}$ |
| --- | --- |
| oral[*1] | No death was observed by the continuous administration of 1000 mg/Kg for one week. |
| intravenous[*2] | >500 mg/Kg |

[*1]administered as tragacanth suspension
[*2]administered as aqueous sodium hydroxide solution Animals used in this test were ten male mice in each route. From the above table, it is clear that the compound of this invention shows low toxicity.

The followings show the examples of the formulation.

(1) Oral drug

| (a) tablet | |
| --- | --- |
| compound A* | 30 mg |
| lactose | 150 mg |
| crystalline cellulose | 50 mg |
| calcium carboxymethylcellulose | 7 mg |
| magnesium stearate | 3 mg |
| Total | 240 mg |
| compound A | 150 mg |
| lactose | 60 mg |
| crystalline cellulose | 30 mg |
| calcium carboxymethylcellulose | 7 mg |
| magnesium stearate | 3 mg |
| Total | 250 mg |

*Compound A of this invention: (2R,4R)-3-[S-[4-Dipropylsulfamoyl)benzoyl]-3-mercaptopropionyl]-2-(2-hydroxyphenyl)-4-thiazolidinecarboxylic acid The tablets may be treated with common film-coating and further with sugar-coating.

| (b) granule | |
| --- | --- |
| compound A | 30 mg |
| polyvinylpyrrolidone | 25 mg |
| lactose | 385 mg |
| hydroxypropylcellulose | 50 mg |
| talc | 10 mg |
| Total | 500 mg |
| (c) powder | |
| compound A | 30 mg |
| lactose | 500 mg |
| starch | 440 mg |
| colloidal silica | 30 mg |
| Total | 1000 mg |
| compound A | 300 mg |
| lactose | 230 mg |
| starch | 440 mg |
| colloidal silica | 30 mg |
| Total | 1000 mg |
| (d) capsule | |
| compound A | 30 mg |
| lactose | 102 mg |
| crystalline cellulose | 56 mg |
| colloidal silica | 2 mg |
| Total | 190 mg |
| compound A | 30 mg |
| glycerin | 349.98 mg |
| butyl p-hydroxybenzoate | 0.02 mg |
| Total | 380 mg |

(2) Injection 1 to 30 mg of compound A is contained in 1 ml of the aqueous solution (ph 6.5-7.0).

SHORT EXPLANATION OF DRAWING

The graphs of FIG. 1 show the antihypertensive effect of the compound of this invention.

In the figure, line 1 is the effect produced by 30 mg/Kg of compound A of this invention; line 2, by 10 mg/Kg of compound A; line 3, by 30 mg/Kg of the reference compound; and line 4, by control.

BEST MODE OF MAKING THE INVENTION

Example 1

(2R,4R)—3—[S—[4—(Dipropylsulfamoyl)benzoyl-]—3—mercaptopropionyl]—2—(2—hydroxyphenyl-)—4—thiazolidinecarboxilic acid 9.7 g of (2R,4R)—2—(2—hydroxyphenyl) —3—(-3—mercaptopropionyl)—4—thiazolidinecarboxylic acid and 12.9 g of potassium carbonate are dissolved in 80 ml of water, and 40 ml of ethyl ether solution of 9.4 g of 4—(dipropylsulfamoyl)benzoyl chloride is added dropwise under ice-cooling. After the addition the reaction mixture is stirred for 1 hour under ice-cooling and for another 1 hour at room temperature. Ether is removed in vacuo and residual solution is adjusted to pH 1 with 6N hydrochloric acid. Produced oily residue is extracted with ethyl acetate. The organic layer is washed with water and dried over anhydrous magnesium sulfate and concentrated in vacuo. The resulting residue is purified by silica gel column chromatography to give 10.5 g of the titled compound as amorphous powder.

$[\alpha]_D^{24}$ +100.6° (c=1.1, methanol).

IR (KBr, cm$^{-1}$)* 3370 (—OH), (—COOH), 1650 (—NCO—), 915 (—SCOph).

NMR (CDCl$_3$,δ) 0.85 (6H, t, J=7.0Hz, C—CH$_3 \times 2$), 1.18—2.00 (4H, m, —CH$_2$—×2), 3.10 (4H, t, J=7.0Hz, —CH$_2$—×2), 2.00-4.00 (6H, m, —CH$_2$CH$_2$—and C$_5$—H$_2$), 4.98 (1H, t, J=6.5Hz, C$_4$—H), 6.32 (1H, s, C$_2$—H), 6.51-7.13 (3H, m, aromatic H), 7.50-8.15 (5H, m, aromatic H), 8.50-9.50 (2H, br s, —OH and —CO$_2$H)

* The same shall be applied hereinafter unless specified.

Example 2

(2R,4R)—3—[S—[4—Benzylsulfonylamino)benzoyl-]—3—mercaptopropionyl]—2—(2—hydroxyphenyl-)—4—thiazolidinecarboxylic acid By using 12.9 g of (2R,4R)—2—(2—hydroxyphenyl-)—3—mercaptopropionyl) —4—thiazolidinecarboxylic acid and 9.3 g of 4—(benzylsulfonylamino)benzoyl chloride in the same procedures as Example 1, 10.9 g of the titled compound is obtained.

mp 121-124°C. (ethonol-water, dec.).

$[\alpha]_D^{26}$ +114.7°(c=0.8, methanol).

IR 1735 (—COOH), 1630 (—NCO—, —SCO—), 1600 (C=C), 910 (—SCOph).

NMR (DMSO—d$_6$,δ)2.97-3.63 (6H, m, —CH$_2$CH$_2$-—and C$_5$—H$_2$), 4.47 (2H, s, —CH$_2$—), 4.82 (1H, t, J=8.0Hz, C$_4$H), 6.40 (1H, s, C$_2$—H), 6.63-8.13 (13H, m, aromatic H), 8.23-10.50 (3H, m, —OH, —CO$_2$H and —NH—).

Example 3

(2R,4R)

—3—(S—Benzoyl—3—mercaptopropionyl)—2—(-2—hydroxyphenyl)—4—thiazolidinecarbohydroxamic acid 3.1 g of N—methylmorpholine is added to 180 ml of dry tetrahydrofuran solution of 12.5 g of (2R,4R)—3—(S—benzoyl—3—mercaptopropionyl) —2—(2—hydroxyphenyl)—4—thiazolidine—carboxylic acid. To the reaction mixture, 4.1 g of isobutyl chlorocarbonate is added dropwise while stirring under ice-cooling and further stirred for 30 minutes at the same temperature. To this suspension, 120 ml of methanol solution containing 6.3 g of hydroxylamine hydrochloride and 3.6 g of sodium hydroxide is added dropwise, and stirred for 2 hours by gradually restoring the room temperature. The solvent is removed in vacuo, and N hydrochloric acid is added to the resulting residue. Separated oil is extracted with ethyl acetate, and the organic layer is washed with saturated sodium chloride solution and dried over anhydrous magnesium sulfate. The solvent is removed in vacuo and the resulting oily residue is purified by silica gel coulumn chromatography to give 6.0 g of the titled compound.

mp 105-110° C. (amorphous powder, dec.).

$[\alpha]_D^{25}$ +159.6°(c=1.1, methanol).

IR (nujol, cm$^{-1}$) 3200 (—OH), 1650 (SCO), 1625 (—NCO—), 912 (—SCOPh).

NMR (DMSO—d$_6$, δ) 3.13 (6H, m, —CH$_2$CH$_2$—and C$_5$—H$_2$), 4.47

(1H, t, J=8.0Hz, C$_4$—H), 6.27 (1H, s, C$_2$—H), 6.50-8.00 (8H, m, aromatic H), 8.20 (1H, d, J=6.0Hz, aromatich H), 8.93 (1H, br s, —CONH—), 9.72 (1H, br s, —OH), 10.70 (1H, br s, N—OH).

Example 4

(2R,4R)—2—(2—Hydroxyphenyl)—3—(3—mercaptopropionyl)—4—thiazolidinecarbohydroxamic acid 60 ml of concentrated ammonia water is added to 50 ml of methanol solution of 4.3 g of (2R,4R)—3—(-S—benzoyl—3—mecaptopropionyl) —2—(2—hydroxyphenyl)—4—thiazolidinecarbohydroxamic acid, and stirred for 1.5 hours at room temperature. Ammonia and methanol are removed in vacuo and extracted with ethyl acetate. The aqueous layer is acidified with concentrated hydrochloric acid and extracted with ethyl acetate. The organic layer is washed with saturated sodium chloride solution, dried over anhydrous magnesium sulfate and concentrated in vacuo.

The resulting oily residue is purified by silica gel column chromatography to give 2.0 g of the titled compound.

mp 90°-96°C. (amorphous powder, dec.).

$[\alpha]_D^{25}$+184.3°(c=0.8, methanol).

IR (nujol, cm$^{-1}$) 3200 (OH), 1630 (NCO).

NMR (DMSO—d$_6$, δ) 2.50-3.17 (6H, m, —CH$_2$CH$_2$-—and C$_5$—H$_2$), 4.47 (1H, t, J=8.0Hz, C$_4$—H), 6.27 (1H, s, C$_2$—H), 6.80 (3H, m, aromatic H), 8.20 (1H, d, J=6.0Hz, aromatic H), 9.00 (1H, br s, —CONH), 9.70 (1H, br s, OH), 10.63 (1H, br s, N—OH).

Example 5

1—[N—[(2R,4R)—[3—(S—Benzoyl—3—mercapto-propionyl)—2—(2—hydroxyphenyl)—4—thiazolidinyl]carbonyl]hydrazino]phtharazine hydrochloride.

By using 12.5 g of (2R,4R)—3—(S—benzoyl—3—mercaptopropionyl) —2—(2—hydroxyphenyl)—4—thiazolidinecarboxylic acid and 5.9 g of hydrarazine hydrochloride in the same procedures as Example 3, 8.9 g of the titled compound is obtained.

mp 164°–168°C. (ethyl acetate, dec.).

$[\alpha]_D^{24}$ +120.5°(c=1.0, methanol).

IR 1655 (SCO), 1630 (NCO), 1598 (C=C), 910 (SCOPh).

NMR (DMSO—$d_6$,δ) 2.90–3.08 (6H, m, —CH$_2$CH$_2$— and C$_5$—H$_2$), 4.82–5.30 (1H, m, C$_4$—H), 6.30 (1H, s, C$_2$—$_H$), 6.48–7.02 (3H, m, aromatic H), 7.27–7.98 (10H, m, aromatic H), 8.08 (1H, d, J=7.0Hz, aromatic H), 8.43 (1H, s, —OH), 8.55 (2H, m, —NHNH—). cl

Example 6

1—[N—[(2R,4R)—2—[2—(2—Hydroxyphenyl)—3—(-3—mercaptopropionyl)
—4—thiazolidinyl]carbonyl]hydrazino]phtharazine By using 6.0 g of 1—[N—[(2R,4R)—[3—(S—benzoyl—3—mercaptopropionyl) —2—(2—hydroxyphenyl)—4—thiazolidinyl]carbonyl]—hydrazino]phtharazine hydrochloride and 60 ml of concentrated ammonia water in the same procedures as Example 4, 2.4 g of the titled compound is obtained.

mp 142°–144°C. (ethyl acetate, dec.).

$[\alpha]_D^{26}$ +91.5°(c=0.6, methanol).

IR 1630 (NCO), 1598 (C=C).

NMR (DMSO—$d_6$, δ) 1.75–2.25 (1H, m, —SH), 2.25–2.98 (4H, m,

—CH$_2$CH$_2$—), 3.08–3.75 (2H, m, C$_5$—H$_2$), 4.77 (1H, t,

J=9.4Hz, C$_4$—H), 6.38 (1H, s, C$_2$—H), 6.58–8.55 (9H, m, aromatic H), 9.25–10.47 (3H, br s, —NHNH—and —OH).

UTILITY IN AN INDUSTRIAL FIELD

The compounds of this invention are novel compounds which are useful therapeutic agent.

What we claim is:

1. A compound of the general formula [I],

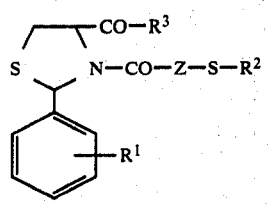

[I]

wherein
$R^1$ is hydrogen, hydroxy, lower alkyl or lower alkoxy;

$R^2$ is hydrogen, benzoyl or

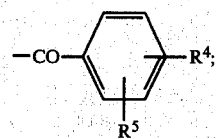

—NHNH—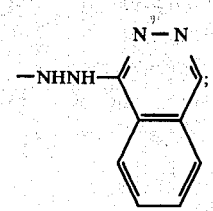;

$R^3$ is hydroxy, lower alkoxy, NHOH or

—SO$_2$N(R$^6$)(R$^7$) or —NHSO$_2$CH$_2$—⟨phenyl⟩;

$R^4$ is
$R^5$ is hydrogen or halogen;
$R^6$ is hydrogen or lower alkyl; $R^7$ is lower alkyl; and
Z is straight or branched lower alkylene containing 1 to 3 carbon atoms;

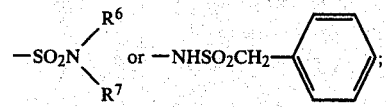

when $R^3$ is hydroxy or lower alkoxy, $R^2$ is
and pharmaceutically acceptable salts thereof, said lower alkyl and lower alkoxy having 1 to 6 carbon atoms.

2. A compound as in claim 1, wherein Z is —CH$_2$CH$_2$—.

3. (2R,4R)—3—[S—[4—(Dipropylsulfamoyl)benzoyl]—3—mercaptopropionyl]—2—(2—hydroxyphenyl)—4—thiazolidinecarboxylic acid as in claim 1.

4. (2R,4R)—3—[S—[4—(Benzylsulfonylamino)benzoyl]—3—mercaptopropionyl]—2—(2—hydroxyphenyl)—4—thiazolidinecarboxylic acid as in claim 1.

5. (2R,4R)—3—(S—Benzoyl—3—mercaptopropionyl)—2—(2—hydroxyphenyl)—4—thiazolidinecarbohydroxamic acid as in claim 1.

6. (2R,4R)—2—(2—Hydroxyphenyl)—3—(3—mercaptopropionyl)—4—thiazolidinecarbohydroxamic as in claim 1.

7. 1—[N—[(2R,4R)—3—[3—(S-Benzoyl—3—mercaptopropionyl)—2—(2—hydroxyphenyl—4—thiazolidinyl]carbonyl]hydrazino]phtharazine as in claim 1.

8. 1—[N—[(2R, 4R)—[2—(2—Hydroxyphenyl)—3—(3—mercaptopropionyl)—4—thiazolidinyl]carbonyl]hydrazino]phtharazine]as in claim 1.

9. Antihypertensive agent comprising an effective amount of a compound of claim 1 together with a pharmaceutical carrier.

10. Antihypertensive agent comprising an effective amount of a compound of claim 2 together with a pharmaceutical carrier.

11. Antihypertensive agent comprising an effective amount of the compound of claim 3 together with a pharmaceutical carrier.

12. Antihypertensive agent comprising an effective amount of the compound of claim 4 together with a pharmaceutical carrier.

13. Antihypertensive agent comprising an effective amount of the compound of claim 5 together with a pharmaceutical carrier.

14. Antihypertensive agent comprising an effective amount of the compound of claim 6 together with a pharmaceutical carrier.

15. Antihypertensive agent comprising an effective amount of the compound 7 together with a pharmaceutical carrier.

16. Antihypertensive agent comprising an effective amount of the compound 8 together with a pharmaceutical carrier.

17. A method for reducing hypertension in a mammal having elevated blood pressure comprising adminstering to said mammal a compound as claimed in claim 1 in an amount effective to reduce the blood pressure of said mammal.

* * * * *

UNITED STATES PATENT AND TRADEMARK OFFICE
CERTIFICATE OF CORRECTION

PATENT NO. : 4,464,371

DATED : August 7, 1984

INVENTOR(S) : Jun-ichi IWAO et al

PAGE 1 of 2 PAGES

It is certified that error appears in the above-identified patent and that said Letters Patent is hereby corrected as shown below:

Column 1, line 25: the structural formula should be removed from this line and should be inserted on line 29, after "$R^2$ is hydrogen, benzoyl or".

line 35: the structural formula should be removed from this line and should be inserted on line 40, after "$R^3$ is hydroxy, lower alkoxy, -NHOH or".

line 45: the structural formula should be removed from this line and should be inserted on line 47, after "$R^4$ is".

line 55: the structural formula should be removed from this line and should be inserted on line 59, after "when $R^3$ is hydroxy or lower alkoxy, $R^2$ is".

Column 5, line 37: after "(-OH)," insert --1735--.

Column 6, line 38: replace "aromatich" with --aromatic--.

Column 8, line 5: the structural formula should be removed from this line and should be inserted on line 9, after "$R^2$ is hydrogen, benzoyl or".

UNITED STATES PATENT AND TRADEMARK OFFICE
CERTIFICATE OF CORRECTION

PATENT NO. : 4,464,371

DATED : August 7, 1984

INVENTOR(S) : Jun-ichi IWAO et al

It is certified that error appears in the above-identified patent and that said Letters Patent is hereby corrected as shown below:

Column 8, line 15: the structural formula should be removed from this line and should be inserted on line 20, after "$R^3$ is hydroxy, lower alkoxy, -NHOH or".

line 25: the structural formula should be removed from this line and should be inserted on line 27, after "$R^4$ is".

line 35: the structural formula should be removed from this line and should be inserted on line 40, after "when $R^3$ is hydroxy or lower alkoxy, $R^2$ is".

line 57: after "thiazolidinecarbohydroxamic" insert --acid--.

Column 10, line 5 (Claim 15): after "compound" insert --of claim--.

line 8 (Claim 16): after "compound" insert --of claim--.

Signed and Sealed this

Eighteenth Day of June 1985

[SEAL]

Attest:

DONALD J. QUIGG

Attesting Officer

Acting Commissioner of Patents and Trademarks